United States Patent [19]

Rider

[11] Patent Number: 4,822,280

[45] Date of Patent: Apr. 18, 1989

[54] DISPENSER FOR LIGHT CURABLE SUBSTANCES

[76] Inventor: John D. M. Rider, 410 Compen Building, 146 Commercial Road, Pietermaritzburg, 3220, South Africa

[21] Appl. No.: 51,135

[22] Filed: May 15, 1987

[30] Foreign Application Priority Data

May 19, 1986 [ZA] South Africa .................... 86/3721

[51] Int. Cl.⁴ .............................................. A61C 5/04
[52] U.S. Cl. ................................. 433/229; 220/345; 206/63.5; 206/368
[58] Field of Search ................. 433/90, 229; 206/63.5, 206/368, 570; 422/102; 220/345, 23.8

[56] References Cited

U.S. PATENT DOCUMENTS 2,022,743 12/1935 Sengbusch .......................... 220/345

2,528,819 11/1950 Cohn et al. ........................ 206/63.5

Primary Examiner—Samuel Scott
Assistant Examiner—Noah Kamen
Attorney, Agent, or Firm—Harness, Dickey & Pierce

[57] ABSTRACT

The invention relates to a dispenser for dispensing light curable substances, such as substances used for various dental applications. The dispenser includes a body defining a dispensing formation, the body and dispensing formation being designed to cooperate with a closure, such as a lid, for closing-off the dispensing formation and thereby isolating light curable substances contained in the dispensing formation from light. A charging opening may also be defined by the body, that leads into the dispensing formation and permits charging of light curable substance into the formation by means of a syringe, or the like, in which these substances are generally contained.

8 Claims, 2 Drawing Sheets

DISPENSER FOR LIGHT CURABLE SUBSTANCES

BACKGROUND AND SUMMARY OF THE INVENTION

This invention relates to a dispenser. More particularly, the invention relates to a dispenser for dispensing light curable substances used for various dental applications.

According to the invention, there is provided a dispenser for dispensing light curable substances, which includes a body;

at least one dispensing formation, into which a light curable substance can be charged from a storage container for dispensing purposes, defined within the body; and closure means for closing off the dispensing formation and isolating any light curable substance therein from light.

The shape and configuration of the body and, in particular, the dispensing formation, may be such that a light curable substance contained therein is easily dispensible therefrom for dental applications by a dentist. As such, the shape and configuration of the dispensing formation may be determined by the particular dental tools whereby substances will be dispensed therefrom.

Hence, in one embodiment of the invention, the body may be in the form of a box with the dispensing formation being in the form of a recess within the box. The recess may be at least partially dish-shaped to facilitate dispensing of light curable substances therefrom for dental applications by a dentist.

The dispenser may include a charging opening in the box, through which the light curable substance can be charged into the recess from a storage container. When the storage container is a storage syringe, the charging opening may be adapted to receive and locate the syringe therein with the end through which the substance can be dispensed from the syringe being in communication with the recess. Preferably, the charging opening may be formed so that a storage syringe can fit frictionally therein in the above defined configuration.

The body may comprise first and second body parts, with the body parts being separable from each other with the recess provided in the first body part and the charging opening in the second body part. The first body part may hence be interchangeable with different second body parts, and these second body parts may be adapted to receive different shapes and sizes of storage syringes therein. The dispenser my thus include a plurality of such second body parts for each body.

The closure means may be a lid pivotally secured to the body and displaceable between an open position, in which access into the dispensing formation is provided for, and a closed position, in which the formation is closed off. The lid may be of an opaque material thereby to isolate any substance contained within the dispensing formation from light when the lid is in its closed position. The lid may be of a flip-top type.

Alternatively, the closure means may be a lid that is slidably displaceable with respect to the body between an open position, in which access into the dispensing formation is provided for, and a closed position, in which the formation is closed off, the lid being of an opaque material thereby to isolate any substance contained within the dispensing formation from light when the lid is in its closed position.

Furthermore, two or more dispensing formations may be provided, in which case the closure means may include separate lids for closing off the individual dispensing formations.

In another embodiment of the invention, the body may be in the form of a drawer, with the closure means being a drawer holder within which the body is slidably receivable, the drawer holder being of an opaque material so that any substance contained within the dispensing formation of the body is isolated from light. The dispenser may include a plurality of bodies each defining at least one of the dispensing formations, and wherein the drawer holder provides for a plurality of drawers to be received therein, the individual bodies being receivable within individual holder formations defined by the drawer holder.

For the configuration in which a storage syringe is receivable within the charging opening, the configuration may be such that the individual bodies in drawer form are receivable within the drawer holder, either with or without a syringe received therein.

It is also anticipated that the body may be connectable to additional similar bodies to form a dispenser for dispensing two or more different light curable substances.

The particular configuration of the closure means may be such that the overall dispenser is also dust proof to thereby protect light curable substances contained within the dispensing formations of the or each body.

The dispenser may also include zones on the body and/or the closure means, the zones being adapted to have suitable markings applied thereto whereby substances contained within the individual bodies can be identified.

BRIEF DESCRIPTION OF THE DRAWINGS

The invention is now described, by way of an example, with reference to the accompanying diagrammatic drawings, in which.

DETAILED DESCRIPTION OF THE PREFERRED EMBODIMENTS

Figure 1:
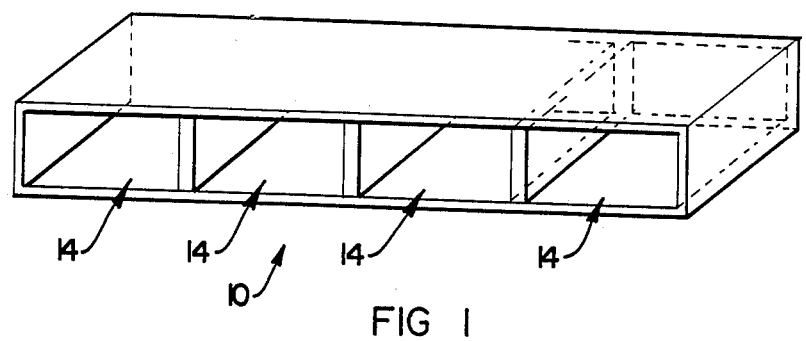
FIG. 1 shows a three-dimensional view of a closure means of a first embodiment of a dispenser, in accordance with the invention.
Figure 2:
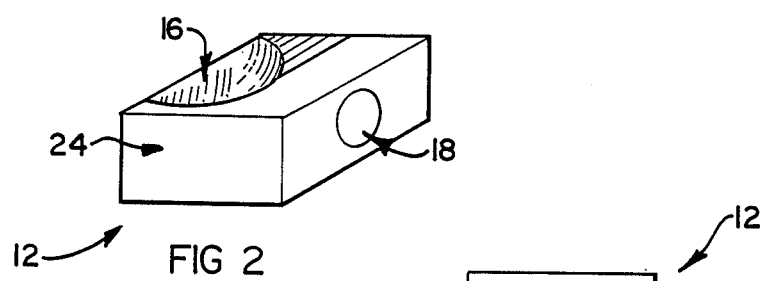
FIG. 2 shows a three-dimensional view of the body of the first embodiment of the dispenser, in accordance with the invention.
Figure 3:
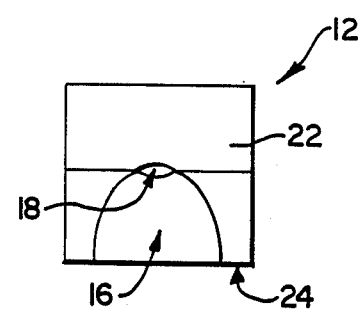
FIG. 3 shows a top plan view of the body of FIG. 2.
Figure 4:
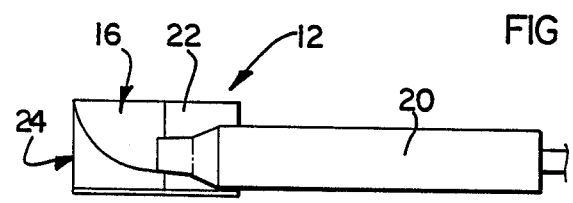
FIG. 4 shows a schematic cross-sectional side view of the body of FIG. 2.

Referring initially to FIGS. 1 to 4 of the drawings, a closure means for a dispenser for dispensing light curable substances, in accordance with the invention, is generally indicated by the reference numeral 10 whereas the body of the dispenser is generally indicated by the reference numeral 12.

The closure means 10 is in the form of a drawer holder defining four open ended drawer compartments 14 within which four separate bodies 12 are slidably receivable in a drawer fashion.

Each body 12 has a dispensing formation 16 which is in the form of a partially dish-shaped recess formed within the body and 12 and into which a light curable substance can be charged, from a storage container, for dispensing purposes. The shape and configuration of the formation 16 is particularly such that dispensing of light curable substances therefrom for dental applications by a dentist is facilitated, dental tools being used for this purpose essentially determining its ideal shape and configuration.

A charging opening 18 leads to the dispensing formation 16 from one end of the body 12, the charging opening 18 being specifically adapted to receive the front end of a storage syringe therein, so that a light curable substance contained within the storage syringe can be discharged from the storage syringe into the formation 16. The configuration of a syringe 20 being located in position within the charging opening 18 is clearly illustrated in FIG. 4.

The body 12 of the dispenser is adapted to fit snugly into a drawer compartment 14 of the closure means 10 and, being of an opaque material, the closure means 10 will thereby completely isolate the dispensing formation 16 and, in particular, any substances contained therein, from light and dust. The configuration of the body 12 within its compartment 14 may particularly be such that the charging opening 18 can retain a storage syringe therein, until fully discharged, the syringe effectively projecting from the closure means 10 in this configuration. The syringe can thus be used as a handle to manipulate the body 12. As such, when held within the closure means 10, any substance contained within a dispensing formation 16 of a body 12 will not cure and can thereby remain usable at any subsequent time when needed.

The closure means 10 specifically provides for a plurality of bodies 12 to fit slidably therein so that a number of different light curable substances can be simultaneously contained therein, this being a requirement of dentists insofar as different substances and/or colour substances are often required to be simultaneously used and/or different substances are required for various different applications.

The benefit of the dispenser of the invention is that any light curable substances discharged from its storage syringe and not immediately used will not require to be disposed of because of the curing effect light may otherwise have thereon when not stored within a suitable location in which it is isolated from light. Also, such substances will not be exposed to dust or other dirt particles which may again render the substance inutile for subsequent applications.

It will be appreciated that the above function can in fact be carried out in various different modes while still providing for the essential principles of the present invention which is to provide for a dispenser within which light curable substances can be contained for extended periods of time while remaining useful for use in various dental applications. For example, the body 12 may be provided with a flip-top type lid or a slidable lid which can cover the dispensing formation 16 and thereby perform the same function. As such, a plurality of dispensing formations 16 can be defined by a single body with each dispensing formation 16 being closable by a separate lid. Also, for the particular configuration shown in the drawings, the body 12 fits into the closure means 10 in a direction in which the opening 18 faces the operative rear end of the closure means 10 but in an alternative configuration (not shown), both the formation 16 and an opening equivalent to the opening 18 may be covered. The body may then be provided with a handle to facilitate its manipulation.

Furthermore, in order to provide for different syringes having different cross-sectional dimensions, the body part 22 of the body 12 may be a removable part being interchangeable with alternative parts adapted to receive different storage syringes. A particular dispenser may thus be provided with a selection of body parts 22.

Figure 5:
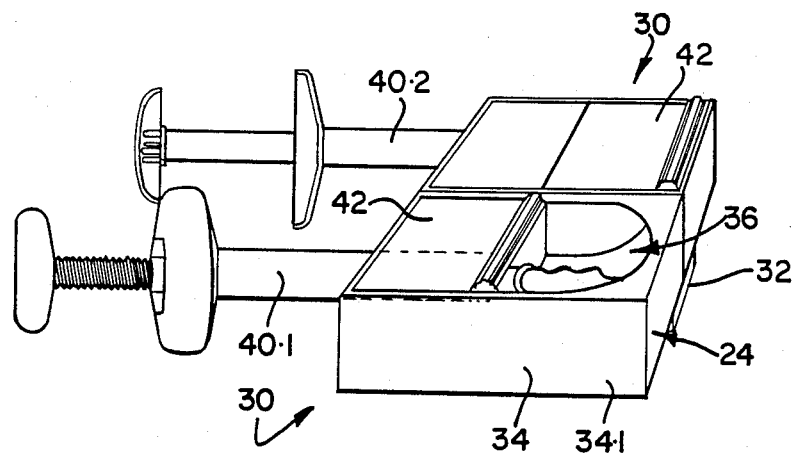
FIG. 5 shows a three-dimensional view of a second embodiment of a dispenser, in accordance with the invention.
Figure 6:
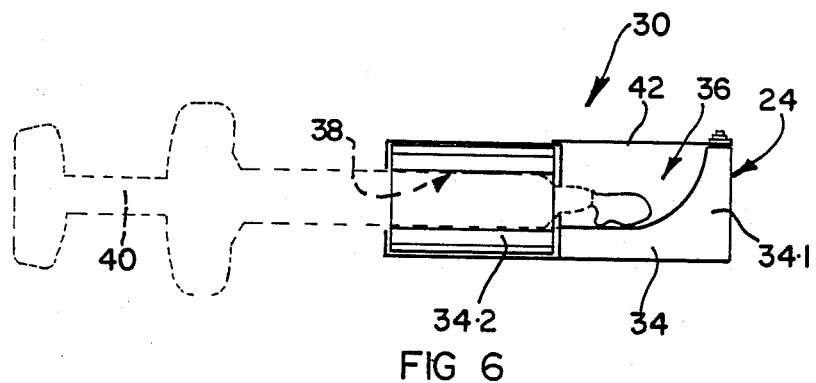
FIG. 6 shows a schematic cross-sectional side view of the dispenser of FIG. 5.
Figure 7:
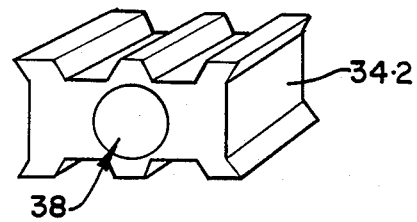
FIG. 7 shows a three-dimensional view of a separable body part of the dispenser of FIG. 5.

In order to illustrate at least some of the above alternatives, a second possible embodiment of the invention is illustrated in FIGS. 5 to 7. Referring to these figures, this second embodiment of a dispenser, in accordance with the invention, is generally indicated by the reference numeral 30. FIG. 5 in fact illustrates two such dispensers 30 that are connected together by a suitable connector piece 32 as will be described in more detail hereafter.

The dispenser 30 includes a body 34 that has a dispensing formation 36 formed therein, the dispensing formation 36 being of a similar shape and configuration as the dispensing formation 16 described above.

The body 34 itself comprises two separable body parts, 34.1 and 34.2 respectively, the body part 34.2 defining a cross-sectional profile as is clearly illustrated in FIG. 7 and fitting slidably into the body part 34.1, that itselfs defines a suitable complementary formation for this purpose.

The body part 34.2 has a charging opening 38 leading therethrough which is in communciation with the dispensing formation 36. The charging opening 38 is again specifically adapted to receive the front end of a storage syringe therein, so that a light curable substance contained within the storage syringe can be discharged from the storage syringe into the formation 16. The configuration of a syringe 40 in position within the charging opening 38 is clearly illustrated in FIGS. 5 and 6.

It will be appreciated that with the body part 34.2 being removable, this part is in fact interchangeable so that different body parts for receiving different syringes can be utilised in conjunction with a particular dispenser 30. FIG. 5 in fact illustrates two dispensers 30 being associated with two different syringes 40.1 and 40.2 respectively, the respective dispensers accordingly having different body parts 34.2 that are specifically adapted to receive the respective syringes 40.

The dispenser 30 further has a closure means in the form of a slidable lid 42 which is slidably displaceable with respect to the body 34 of the dispenser 30 between open and closed positions as are clearly illustrated in FIGS. 5 and 6. In its open position, the lid 42 provides access to the dispensing formation 36 for dispensing of a light curable substance from the dispensing formation. Clearly, the body 34 may be specifically adapted to receive the lid 42 and permit slidable displacement thereof between its open and closed positions.

As is clearly illustrated and mentioned above, two or more dispensers 30 can be connected together by a connector piece 32 so that two or more different light curable substances can be simultaneously dispensed from a "single" unit comprising two or more dispensers that are suitably connected together. For example, for dental applications, it is often necessary to mix two light curable substances in order to provide a substance having a suitable colour, as may be required for specific applications.

It will again be appreciated that the syringes 40 can be utilised as a means for manipulating dispensers 30. Also, with the bodies 34 and lids 42 being of opaque materials, it is believed that dispensers 30 can be effectively used to contain light curable substances in a non-cured form for extended periods, as can the dispenser described hereinabove with reference to FIGS. 1 to 4. Once again, light curable substances contained within the dispenser 30 will again not be exposed to dust or other dirt particles which can render such substances inutile.

Both embodiments of the dispenser described above may include zones, for example end walls 24, that can be utilized for applying markings to the dispenser whereby substances contained therein can be identified. Clearly, the zones may be defined by any part of the bodies 12, 34 and/or parts associated therewith. Alternative means may clearly also be provided for this purpose.

I claim:

1. A dispenser for dispensing light curable substances, which includes:
   a body in the form of a box;
   at least one dispensing formation into which a light curable substance can be charged from a storage container for dispensing purposes, said dispensing formation being in the form of a recess within said box, said recess being at least partially dish-shaped to facilitate dispensing of said light curable substance therefrom for dental applications by a dentist;
   closure means for closing off said dispensing formation and isolating any light curable substance therein from light; and
   means for locating and holding said storage container within said body during and subsequent to charging, said locating and holding means including a charging opening in the box through which said light curable substance can be charged into said recess from said storage container, said storage container being a storage syringe, with said charging opening being adapted to receive, locate and hold said syringe body therein, with the end through which said substance can be dispensed from the syringe being in communication with said recess.

2. A dispenser as claimed in claim 1, wherein the closure means is a lid that is slidably displaceable with respect to the body between an open position, in which access into the dispensing formation is provided for, and a closed position, in which the formation is closed off, the lid being of an opaque material thereby to isolate any substance contained within the dispensing formation from light when the lid is in its closed position.

3. A dispenser according to claim 1, wherein the body is in the form of a drawer, with the closure means being a drawer holder within which the body is slidably receivable, the drawer holder being of an opaque material so that any substance contained within the dispensing formation of the body is isolated from light.

4. A dispenser as claimed in claim 1, in which the body is connectable to additional similar bodies to form a dispenser for dispensing two or more different light curable substances.

5. A dispenser as claimed in claim 1, which includes at least one zone on the body and the closure means, the zone being adapted to have suitable markings applied thereto whereby substances contained within the body can be identified.

6. A dispenser for dispensing light curable substances, which includes:
   a body;
   at least one dispensing formation, into which a light curable substance can be charged from a storage container for dispensing purposes, defined within the body; and
   closure means for closing off the dispensing formation and isolating any light curable substance therein from light, said body being in the form of a box with the dispensing formation being in the form of a recess within the box, said dispensing further including a charging opening in the box, through which the light curable substances can be charged into the recess from a storage container, said storage container being a storage syringe, with the charging opening being adapted to receive and locate the syringe therein, with the end through which the substance can be dispensed from the syringe being in communication with the recess, the body including first and second body parts, the body parts being separable from each other with the recess provided in the first body part and the charging opening in the second body part, with the first body part being adapted to interchangeably locate different second body parts with respect thereto, and these second body parts being adapted to receive different shapes and sizes of storage syringes therein.

7. A dispenser as claimed in claim 6, which includes a plurality of different configuration second body parts.

8. A dispenser as claimed in claim 7, which includes a plurality of bodies each defining at least one of the dispensing formations, and wherein the drawer holder provides for a plurality of drawers to be received therein, the individual bodies being receivable within individual holder formations defined by the drawer holder.

* * * * *

UNITED STATES PATENT AND TRADEMARK OFFICE
CERTIFICATE OF CORRECTION

PATENT NO. : 4,822,280
DATED : April 18, 1989
INVENTOR(S) : John D. M. Rider

It is certified that error appears in the above-identified patent and that said Letters Patent is hereby corrected as shown below:

Col. 1, Line 53   "my" should be --may--

Col. 3, Line 5    delete "and" (first occurrence)

Col. 6, Line 31   "substances" should be --substance--

Signed and Sealed this

Twenty-seventh Day of March, 1990

Attest:

JEFFREY M. SAMUELS

*Attesting Officer*                *Acting Commissioner of Patents and Trademarks*